(12) United States Patent
Qiao

(10) Patent No.: US 11,660,139 B2
(45) Date of Patent: May 30, 2023

(54) ELECTROPORATION PROBE

(71) Applicant: Yang Qiao, Pearland, TX (US)

(72) Inventor: Yang Qiao, Pearland, TX (US)

(73) Assignee: RADIOCLASH INC., Houston, TX (US)

( * ) Notice: Subject to any disclaimer, the term of this patent is extended or adjusted under 35 U.S.C. 154(b) by 380 days.

(21) Appl. No.: 16/843,406

(22) Filed: Apr. 8, 2020

(65) Prior Publication Data

US 2020/0323583 A1  Oct. 15, 2020

Related U.S. Application Data

(60) Provisional application No. 62/862,943, filed on Jun. 18, 2019, provisional application No. 62/832,197, filed on Apr. 10, 2019.

(51) Int. Cl.
*A61B 18/14* (2006.01)
*A61B 18/00* (2006.01)

(52) U.S. Cl.
CPC ........ *A61B 18/1487* (2013.01); *A61B 18/149* (2013.01); *A61B 2018/00083* (2013.01); *A61B 2018/00613* (2013.01)

(58) Field of Classification Search
CPC ............ A61B 18/1477; A61B 18/1487; A61B 18/149; A61B 2018/00083;

(Continued)

(56) References Cited

U.S. PATENT DOCUMENTS 5,472,441 A * 12/1995 Edwards ............ A61B 18/1482
606/49
5,704,908 A   1/1998 Hofmann et al.
(Continued)

FOREIGN PATENT DOCUMENTS

EP        2701791        3/2014
WO    WO 2016/145085    9/2016
(Continued)

OTHER PUBLICATIONS

Burkart et al. "Improving therapeutic efficacy of IL-12 intratumoral gene electrotransfer through novel plasmid design and modified parameters", Gene Therapy, 25, dated (Mar. 9, 2018), pp. 93-103.

(Continued)

*Primary Examiner* — Michael F Peffley
(74) *Attorney, Agent, or Firm* — Eric P. Mirabel

(57) ABSTRACT

An electroporation probe that includes an injection means, allowing a single electroporation probe to be used for both the electroporation of cells and the injection of a fluid. The electroporation probe having (a) a probe body having an interior channel, a first end, and a second end; (b) a plurality of perforations in the probe body proximal the second end; (c) a sleeve positioned within the interior channel, wherein the sleeve is moveable between a first position sealing the perforations and a second position opening the perforations; (d) a connection between the probe body and an electroporation machine, wherein the probe body is in electrical communication with the electroporation machine; and (e) a tubing in fluid communication with the interior channel, wherein fluid injected into a proximal end of the tubing is exitable through the perforations when the sleeve is in the second position.

26 Claims, 14 Drawing Sheets

(58) Field of Classification Search
CPC .. A61B 2018/00107; A61B 2018/0016; A61B 2018/00202; A61B 2018/00613; A61B 2018/143
See application file for complete search history.

(56) References Cited

U.S. PATENT DOCUMENTS

| | | | |
|---|---|---|---|
| 6,068,653 A * | 5/2000 | LaFontaine | A61N 1/04 606/41 |
| 6,071,280 A * | 6/2000 | Edwards | A61B 18/1482 606/41 |
| 6,912,417 B1 | 6/2005 | Bernard et al. | |
| 7,160,296 B2 * | 1/2007 | Pearson | A61B 18/1477 606/42 |
| 7,412,284 B2 | 8/2008 | Hofmann | |
| 8,209,006 B2 | 6/2012 | Smith et al. | |
| 9,020,605 B2 | 4/2015 | McCluskey et al. | |
| 9,233,241 B2 * | 1/2016 | Long | A61B 18/1492 |
| 9,289,606 B2 * | 3/2016 | Paul | A61B 18/14 |
| 10,639,096 B2 * | 5/2020 | Cohen | A61N 7/00 |
| 2005/0048651 A1 | 3/2005 | Ryttsen et al. | |
| 2006/0264752 A1 | 11/2006 | Rubinsky et al. | |
| 2010/0298761 A1 | 11/2010 | Staal et al. | |
| 2013/0110099 A1 * | 5/2013 | Groves | A61M 25/007 606/21 |
| 2015/0366546 A1 | 12/2015 | Kamen et al. | |
| 2020/0305946 A1 * | 10/2020 | DeSimone | A61N 1/327 |

FOREIGN PATENT DOCUMENTS

| | | |
|---|---|---|
| WO | WO 2016/161201 | 10/2016 |
| WO | WO 2018/057943 | 3/2018 |

OTHER PUBLICATIONS

International Search Report and Written Opinion for PCT/US2019/030437 dated Sep. 10, 2019.

Weaver et al. "A brief overview of electroporation pulse strength-duration space: A region where additional intracellular effects are expected", Bioelectrochemistry, 87, dated (Oct. 2012), pp. 236-243.

* cited by examiner

ELECTROPORATION PROBE

CROSS-REFERENCE TO RELATED APPLICATIONS

The present application claims priority under 35 U.S.C. 119(e) to U.S. Provisional Application 62/832,197 filed Apr. 10, 2019 and to U.S. Provisional Application 62/862,943, filed Jun. 18, 2019, both of which are hereby incorporated by reference in their entirety.

BACKGROUND OF THE INVENTION

Field of the Invention

The present invention relates to an electroporation probe that includes an injection means, allowing a single electroporation probe to be used for both the electroporation of cells and the injection of a fluid.

Description of the Related Art

Irreversible electroporation is a treatment modality used for a variety of diseases including but not limited to various types of cancers. A current flowing through two or more probes inserted within a tumor region generates a voltage differential and corresponding field strength. Permanent or temporary pores will be created within the cellular membranes of the tumor region in which the probes are inserted, depending on the electrical field strength.

A higher electrical field strength causes cellular membrane pores created by electroporation to become permanently open, leading to loss of homeostasis within the cells, and corresponding cell death. This type of electroporation is a type of non-thermal ablation called irreversible electroporation. A lower electrical field strength, causes cellular membrane pores to become temporarily open and eventually reseal, leading to no loss of homeostasis, and no corresponding cell death. This event is called reversible electroporation. The phenomenon of reversible electroporation has been used in the past for the treatment of a variety of diseases by allowing for the delivery of medications and materials into cells that are temporarily permeabilized.

Probes inserted into a tumor region and programmed to a high electrical field strength can cause both irreversible electroporation to occur in regions closer in proximity to the probes, and reversible electroporation to occur in regions further away from the probes, due to differences in electrical field strength in relation to the location of the probes.

Combination electroporation therapy (CET) is a new treatment modality that utilizes a high electrical field strength to cause irreversible electroporation to cells in closer proximity to the probes, while simultaneously injecting a medication or material into the tumor region to allow for increased cellular uptake in tumor regions further away from the probes that have had their cellular membranes temporarily permeabilized via the reversible electroporation procedure.

Preclinical studies have found combination electroporation therapy to be more effective at inducing tumor cell death than either irreversible electroporation or intratumoral injection of chemotherapy alone in various types of human cancer cell lines including but not limited to liver cancer, pancreatic cancer, head and neck cancer, brain cancer, and secondary metastases; and utilizing a variety of materials including but not limited to various types of chemotherapy, immunotherapy, genetic material, contrast agents, and nanoparticles. The efficaciousness of the results from preclinical experiments is suggestive of combination electroporation therapy as a promising future gold-standard therapy for the treatment of various diseases.

Probes inserted into a tumor region or other tissue region (such as a draining lymph node) and programmed to a high electrical field strength can cause the release of local inflammatory factors as well as antigens and epitopes from the region of tissue undergoing electroporation. The release of inflammatory factors activates the innate immune response, while the release of antigens and epitopes can lead to the sensitization of cells involved in the adaptive immune response, including but not limited to cytotoxic T Cells and helper T Cells. Sensitization of adaptive immune response cells to these released tissue antigens and epitopes has been shown to cause the maturation of adaptive immune response cells that target and destroy the tumors from which these antigens and epitopes are released.

Matured adaptive immune response cells can destroy both the local tumor, and also circulate throughout the body and target metastatic tumor and cancer cells that share antigens and epitopes with the original tumor that had undergone electroporation in a phenomenon called the abscopal effect. The above explained process is the basis of tumor vaccines. Additionally, when immunotherapies including but not limited to immune checkpoint inhibitors (ex: CTLA-4 inhibitors, PD-1 inhibitors, PD-L1 inhibitors), pro-inflammatory cytokines, oncolytic viruses, bacteria, antigen presenting cells, or other forms of immunotherapy are injected either systemically or locally, the pro-inflammatory immune process is up-regulated, leading to an increase in tumor antigen presentation by innate immune cells, and subsequently an increase in the amount of circulating adaptive immune cells that are sensitized and targeted towards the antigens and epitopes released from the tumor regions that have undergone electroporation.

Currently, combination electroporation therapy is performed via the insertion of separate electroporation probes and injection needles, leading to at least two sites of object insertion into a patient. Multiple insertion sites lead to an increased potential for complications including but not limited to bleeding, infection, and damage to adjacent structures; as well as increased patient discomfort, pain, and suffering. Multiple insertion sites also lead to ergonomic and ease of performance difficulties by the operator.

Therefore, there is a need in the art for a single device that delivers both electroporation and injection via a single instrument to address these issues. There exists a need for improved devices and methodologies to perform combination electroporation therapy.

SUMMARY OF THE INVENTION

The present invention relates to an electroporation probe that includes an injection means, allowing a single electroporation probe to be used for both the electroporation of cells and the injection of a fluid.

One embodiment of the present invention is an electroporation probe comprising: (a) a probe body having an interior channel, a first proximal end, and a second distal end; (b) a plurality of perforations passing through the probe body; (c) a sleeve positioned within the interior channel, wherein the sleeve is moveable between a first position sealing the perforations from the interior channel and a second position opening the perforations to the interior channel; and (d) a fluid channel in fluid communication with the interior channel and a lumen of a tubing, wherein whenever the sleeve is in the second position a fluid injected though the lumen of the tubing is exitable through the perforations in the probe body.

Another embodiment of the present invention is an electroporation device comprising: (a) an electroporation probe having (i) a probe body with an interior channel, a first proximal end, and a second distal end, (ii) a plurality of perforations passing through the probe body, (iii) a sleeve positioned within the interior channel that is moveable between a first position sealing the perforations from the interior channel and a second position opening the perforations to the interior channel, and (iv) an electrode embedded in the probe body; and (b) a tubing having a lumen; (c) an electroporation machine; and (d) a connector housing connected to the electroporation machine at a first end and to the tubing at a second end, wherein the connector housing has a connection point that is mateable to the probe body such that whenever the probe body is mated to the connection point the electroporation machine is in electrical communication with the electrode embedded in the probe body and the tubing is in fluid communication with the interior channel.

Yet another embodiment of the present invention is an electroporation device comprising: (a) an electroporation probe having (i) a probe body having an interior channel, a first proximal end, and a second distal end, (ii) a plurality of perforations passing through the probe body, (iii) a sleeve positioned within the interior channel that is moveable within the interior channel between a first position sealing the perforations from the interior channel and a second position opening the perforations to the interior channel, and (iv) an electrode embedded in the probe body; (b) a connector housing having a point of attachment for the probe; (c) an electroporation machine in electrical communication with the electroporation probe whenever the probe is attached to the point of attachment of the connector housing; and (d) a tubing in fluid communication with the interior channel of the probe whenever the probe is attached to the point of attachment of the connector housing.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. The foregoing has outlined rather broadly several aspects of the present invention in order that the detailed description of the invention that follows may be better understood.

BRIEF DESCRIPTION OF THE DRAWINGS

Appended FIGS. 1-13 depict certain non-limiting embodiments of a combination electroporation and injection probe. The figures are not intended to limit the scope of the invention but, instead, are intended to provide depictions of specific embodiments, features and non-limiting characteristics of the systems described herein. The accompanying figures further illustrate the present invention. The components of an embodiment shown in the drawings are not necessarily drawn to scale, emphasis instead being placed upon clearly illustrating the principles of the present invention.

FIG. 1 illustrates a cross-sectional view just below the outer surface of one embodiment of an electroporation probe showing electrode wires embedded within the probe body and the location of perforations in the probe body.

FIG. 2 is a cross-sectional view of the probe showing how the electrode wires are physically-embedded within the walls of the device probe.

FIG. 3 is a cross-sectional view of the probe, demonstrating the mechanism by which the sleeve separates the internal chamber of the device from the perforations.

FIG. 4 is a cross-sectional view demonstrating one embodiment of the connection between the external tubing and the internal chamber, the coating of selected surfaces with a non-conductive material, and the spatial relationship between the tubing and the electrode wires.

FIG. 6 is a cross-section of the probe shown in FIG. 5A along its diameter demonstrating the sleeve in the "closed" position sealing the perforations from the internal chamber of the probe.

FIG. 7 is a cross-section of the probe shown in FIG. 5C along its diameter demonstrating the sleeve in the "open" position allowing fluid communication between the internal chamber and the perforations.

FIG. 10 is a view of a device containing multiple probes showing the location of the electrode wires embedded within the probe in relation to the location of perforations.

FIG. 11 is a cross-sectional view of a device containing multiple probes showing how the electrode wires are physically embedded within the walls of the device probe and connect with the electrodes in the connector housing.

DESCRIPTION OF THE PREFERRED EMBODIMENTS

Figure 1:
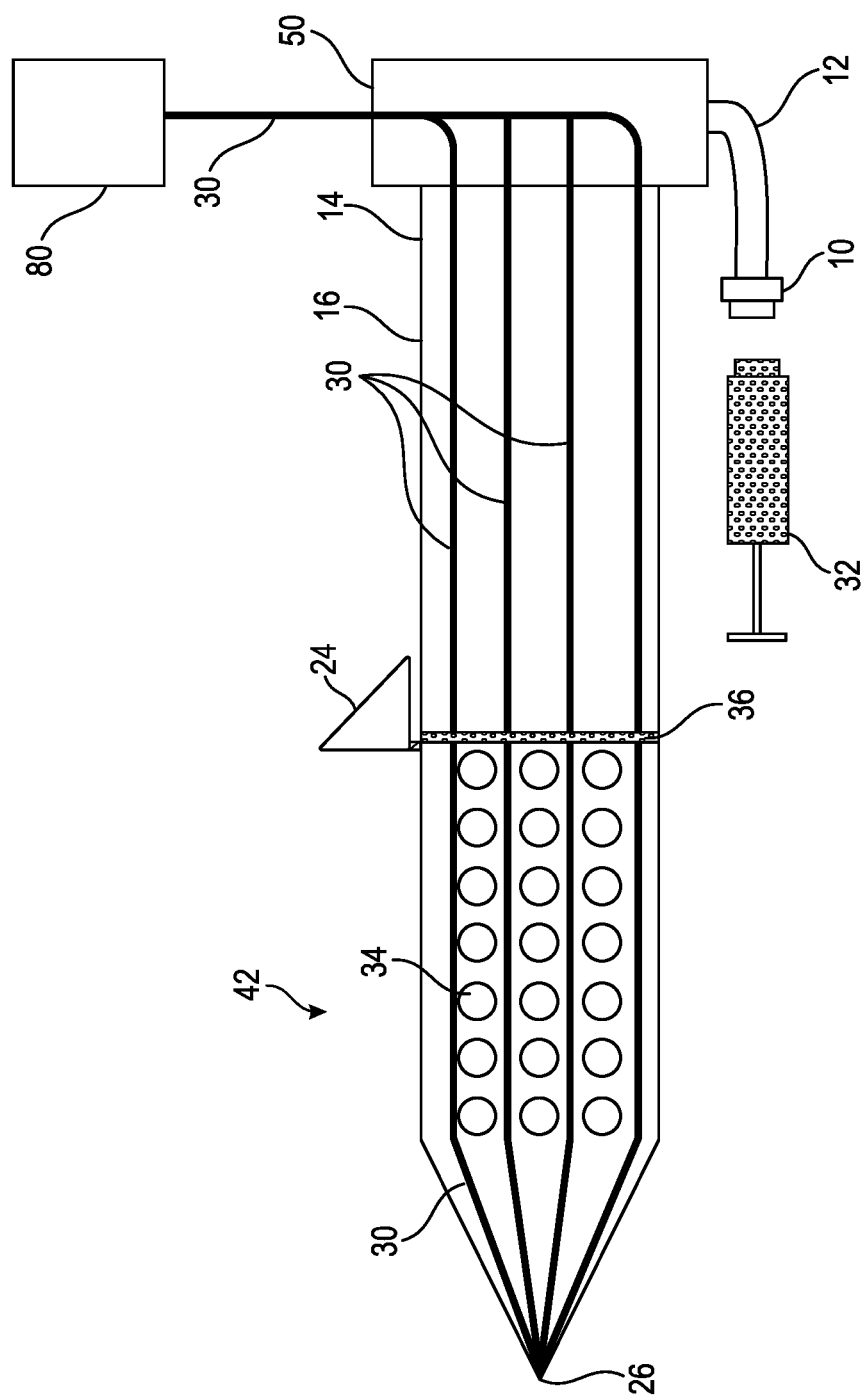

While the specification concludes with the claims particularly pointing and distinctly claiming the invention, it is believed that the present invention will be better understood from the following description. The present invention can comprise or consist essentially of the components of the present invention as well as other ingredients or elements described herein. As used herein, "comprising" means the elements recited, or their equivalent, plus any other element or elements which are not recited. The terms "having," "including," and "comprised of" are also to be construed as open ended unless the context suggests otherwise.

Furthermore as used herein, the term "about" refers to a +/−10% variation from the nominal value. It is to be understood that such a variation is always included in a given value provided herein, whether or not it is specifically referred to. All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. This includes, at the very least, the degree of expected experimental error, technique error and instrument error for a given technique used to measure a value.

As used herein, the term "internet of things" is a system of interrelated computing devices, mechanical and digital machines provided with unique identifiers and the ability to transfer data over a network without requiring human-to-human or human-to-computer interaction or the interconnection via the internet of embedded applications in devices that enables those devices to send and receive data from other devices.

The present invention relates to an electroporation device and its method of use. Preferred embodiments of the electroporation probe include an injection means, allowing a single electroporation probe to be used for both the electroporation of cells and the injection of a fluid.

The Electroporation Device

The electroporation device includes at least one electroporation probe that may also be used as an injection device, allowing for the selected electroporation and/or injection of a fluid from the same probe. The described electroporation device may include, but is not limited to, one or multiple probes, direct or remote connection to a machine that controls the operation of the device such as for electroporation activity, an external tubing that connects to an interior bore of a sleeve positioned within an internal chamber or channel, a probe body having a plurality of perforations that can be selectively covered or exposed, a radio-opaque marker 36, and a sharp tip allowing for the penetration of tissues.

This device facilitates a disease treatment option called combination electroporation therapy, in which an electrical current is used in combination with the injection of a material to augment cellular uptake of the material and/or induce an augmented inflammatory response, and improve the efficacy of treatment of the disease process. This device minimizes the amount of objects such as separate probes and needles that are required for performing combination electroporation therapy, which can decrease the risk of complications such as bleeding, infection, and damage to adjacent structures; decrease patient discomfort, pain, and suffering; and improve the ergonomics and ease-of-performance for the operator.

Embodiments of the electroporation probe described herein include an injection means, allowing a single electroporation probe to be used for both the electroporation of cells and the injection of a fluid. One embodiment of an electroporation probe 42 includes a probe body 16 having an interior channel 20, a first proximal end 14, and a second distal end 26; a plurality of perforations 34 in the probe body closer to the second end than the first end; a sleeve 22 positioned within the interior channel 20, wherein the sleeve 22 is moveable between a first position sealing the perforations and a second position opening the perforations; a connection, such as an electrode wire 30, between the probe body and an electroporation machine 80, wherein the probe body 16 is in electrical communication with the electroporation machine through an electrode passing from the electroporation machine through a connector housing 50 and to an electrode embedded in the probe body; and a tubing 12 in fluid communication with the interior channel 20, wherein a fluid injected into a proximal end of the tubing 12 is exitable through the perforations 34 when the sleeve 22 is in the second position.

Figure 2:
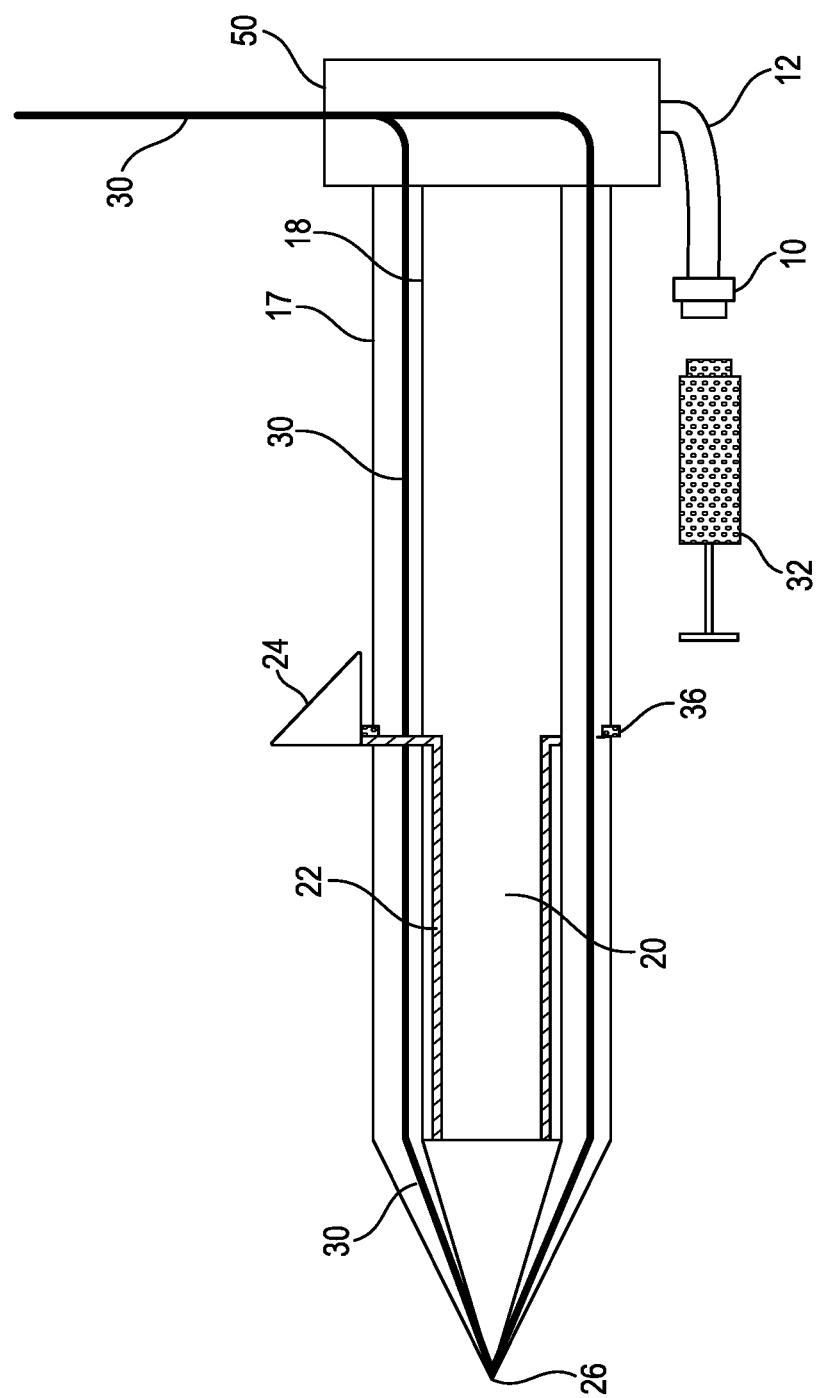
Figure 3:
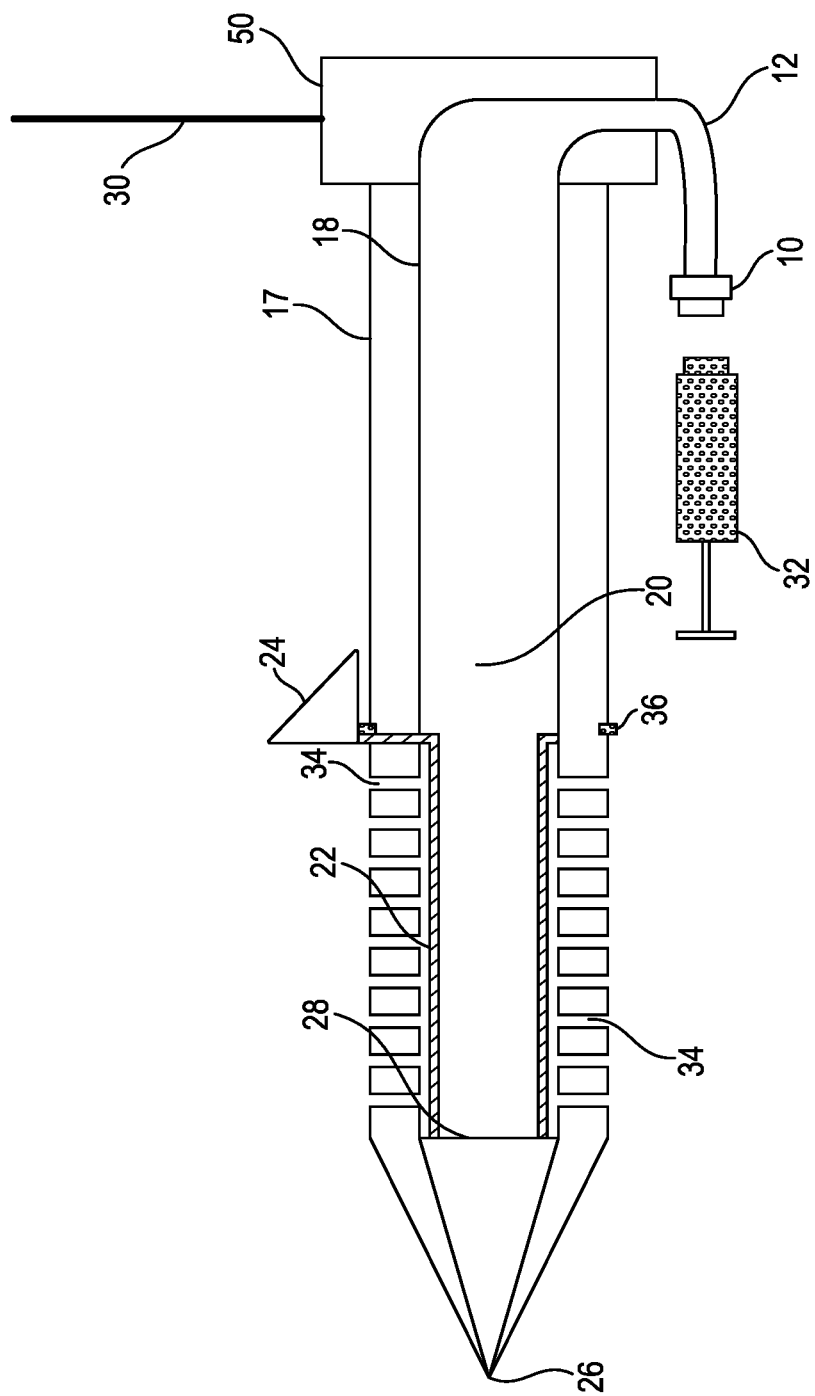

An embodiment of an electroporation probe 42 illustrated in FIGS. 1, 2, and 3 includes a probe 42 having a probe body 16, an internal chamber 20 (also referred to herein as an interior channel), a moveable sleeve 22, a connector housing 50, an electrode wire 30 that provides an electrically transmissive connection between the probe body 16 and an electroporation device 80, and a tubing 12 that provides a fluid connection between a syringe 32 and the internal chamber 20. A more detailed description of the components of the electroporation probe is given below.

Electroporation Probe Body

The probe body 16 is typically elongated from a first (proximal) end 14 to a second (distal) end 26. The probe body has an interior surface 18, an exterior surface 17, and an interior channel/internal chamber 20. The probe body also has multiple perforations 34 that pass through the probe body 16 to connect the internal chamber 20 with the area surrounding the probe exterior surface 17 whenever the sleeve 22 is in its second position opening the perforations.

The probe body 16 is generally made of an electronically conductive material that contains one or more electrodes 30 embedded within the probe body. The electrodes 30 are connected to an electroporation device 80 and generally provide either a positive or a negative charge to the probe body 16. The electrodes run through the probe body substantially the entire length of the probe body. The specific location of charge along the length of the probe may be determined by covering certain sections of the probe body and/or the electrodes with an electronically non-conductive material such as an elastomer. Several examples of using a non-conductive coering are illustrated in FIG. 4 and described below.

Figure 4:
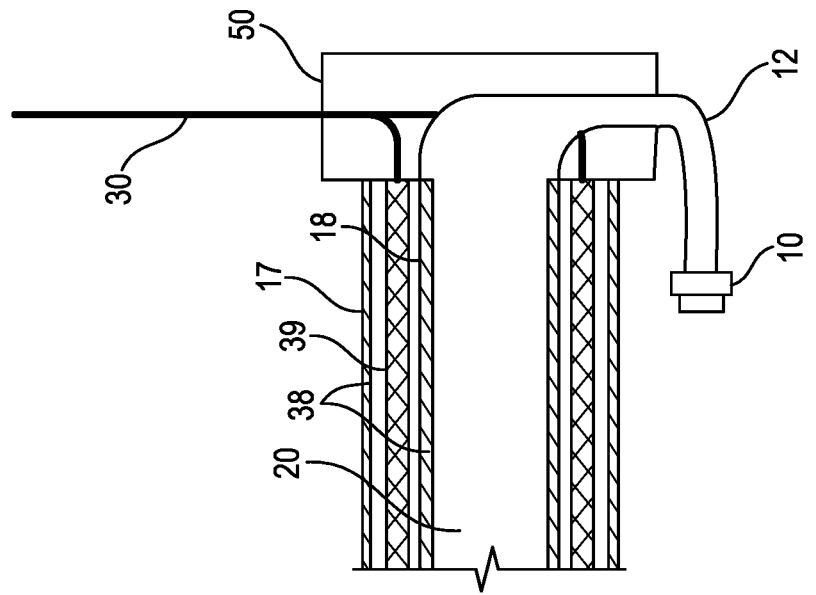
Figure 4:
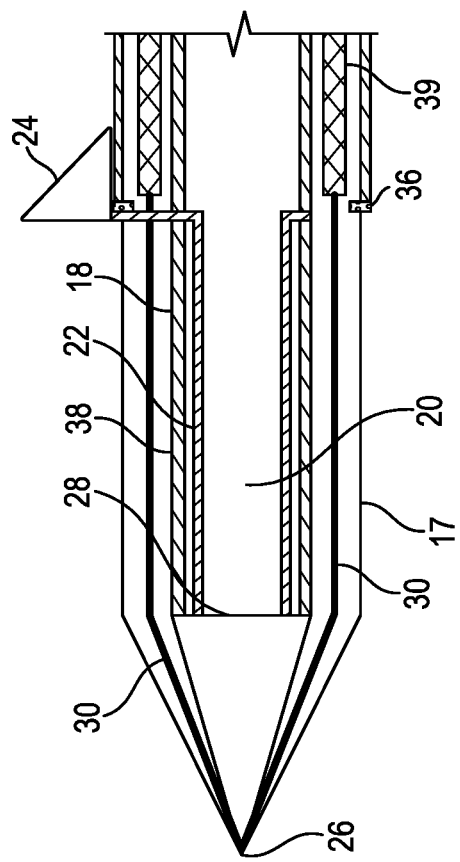

For example, one embodiment of the probe body 16 may have the entire interior surface 18 covered with a substantially inert and/or non-conductive material 38 as shown in FIG. 4. Other embodiments of the probe body 16 may have the outer perimeter of the perforations 34 covered with a similar substantially inert and/or non-conductive material 38. By covering these surfaces of the probe body 16, any material flowing through the internal chamber 20, through the perforations, and out into the tissue surrounding the probe body will be isolated from the charged surface of the probe body.

Other embodiments of the probe body will cover a set region of the exterior surface 17 of the probe body with a non-conductive material 38. For example, the exterior surface 17 of the probe body may be covered from the proximal or top end of the probe body to a point adjacent the top of the perforations 34 or adjacent to the radio-opaque marker 36. Covering the exterior surface 17 of the probe body to a designated position on the probe body, preferably just above the perforations, will prevent the electroporation of the tissue surrounding the probe above the perforations such as illustrated in FIG. 4.

In another embodiment of the probe, a segment of the electrodes embedded in the probe body may be insulated with a substantially inert and/or non-conductive material 38 that is resistant to an electric current. The insulated electrodes 39 will preferably extend from the proximal or top end of the probe body to a point adjacent the top of the perforations 34 or adjacent to the radio-opaque marker 36 as illustrated in FIG. 4.

Yet another embodiment of the probe body will have a radio-opaque marker 36 at a set position along the length of the probe body. This radio-opaque marker 36 is used to visualize the placement of the probe in the tissue to be electroporated. A preferred embodiment of the probe body 16 will have the radio-opaque marker encircling the exterior surface of the probe body just above the perforations 34. Thus, the radio-opaque marker 36 allows for the visualization of the proximal limit of where the perforations 34 begin on the probe under radiographic imaging guidance. This will enable the operator to be sure that the probe has entered the tissue sufficiently to allow the complete injection of the fluid into the tissue.

Perforations

The perforations 34 can be of a variety of different sizes, shapes, quantities, and qualities including but not limited to circles, ovals, squares, rectangles, triangles, pentagons, hexagons, polygons, and slits that may be situated at any distance away from each other, and may also span substantially the entire circumference of the probe. Although the perforations 34 on a single probe 42 may be homogeneous, the perforations on a single probe may alternatively be a heterogeneous mixture of many different sizes, shapes, quantities, and qualities.

The perforations will typically be vertically or horizontally aligned. One embodiment of multiple perforations 34 is shown in FIGS. 1 and 3. The illustrated embodiment shows multiple vertically aligned and parallel rows of perforations 34 spaced at a distance from each other around the circumference of the probe body 16. Preferably, the perforations are located close to the distal or second end 26 of the probe body and adjacent to the bottom 28 of the interior channel 20.

Moveable Sleeve

The perforations 34 may be selectively exposed or covered via a moveable sleeve 22. Typically, an operator of the electroporation/injection device will want to close or seal the perforations of a probe being used for electroporation when a charge is being delivered through the probe. In contrast, whenever it is desired to inject a fluid at the electroporation site, the perforations should be open for the delivery of the fluid into the tissue.

The perforations 34 are selectively opened or sealed using a moveable sleeve, wherein the sleeve is movable between a first position sealing the perforations and a second position opening the perforations. The movement of the sleeve 22 can be executed using a multitude of mechanisms such as a sliding mechanism; a clicking mechanism; a rotational mechanism; or a button located on the external surface of the probe that activates an electrical, magnetic, mechanical, or internet-of-things mechanism to move the sleeve within the internal chamber 20 of the probe body 16 between the first and second position of the sleeve.

The sleeve 22 can also be moved between the first position and the second position using an external remote control device that activates an electrical, magnetic, mechanical, or internet-of-things mechanism. The sleeve can also be moved between a first and second position using a wire or connector tethered to the probe that activates an electrical, mechanical, magnetic, or an internet-of-things mechanism within the interior of the probe body. Alternatively, perforations 34 may be exposed constantly to the environment without a mechanism for covering them up.

Figure 5A:
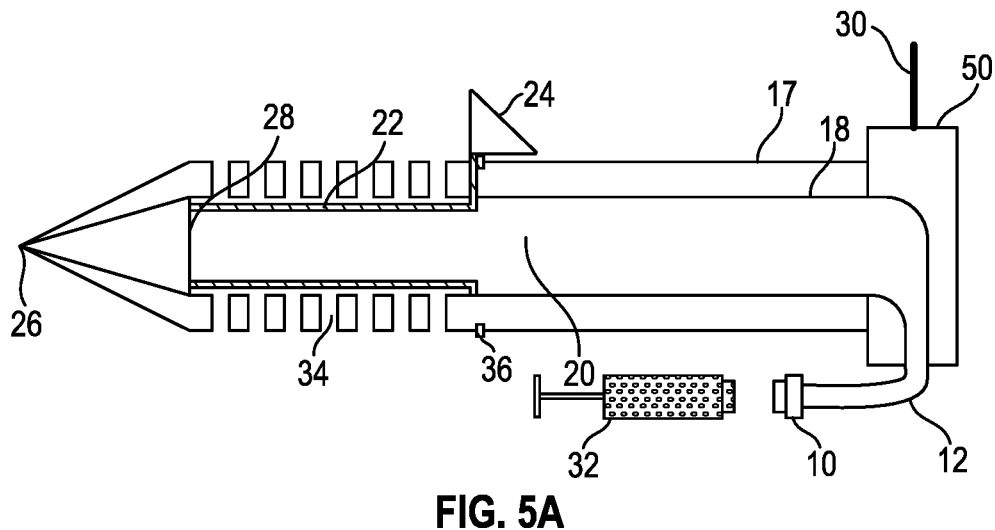
FIGS. 5A-5C demonstrate one embodiment of how the vertical movement of the sleeve allows for exposure of the internal chamber to the perforations.
Figure 5B:
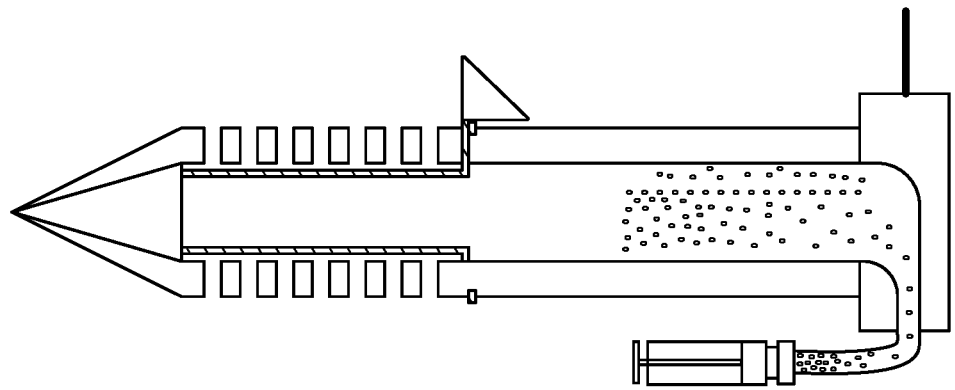
Figure 5C:
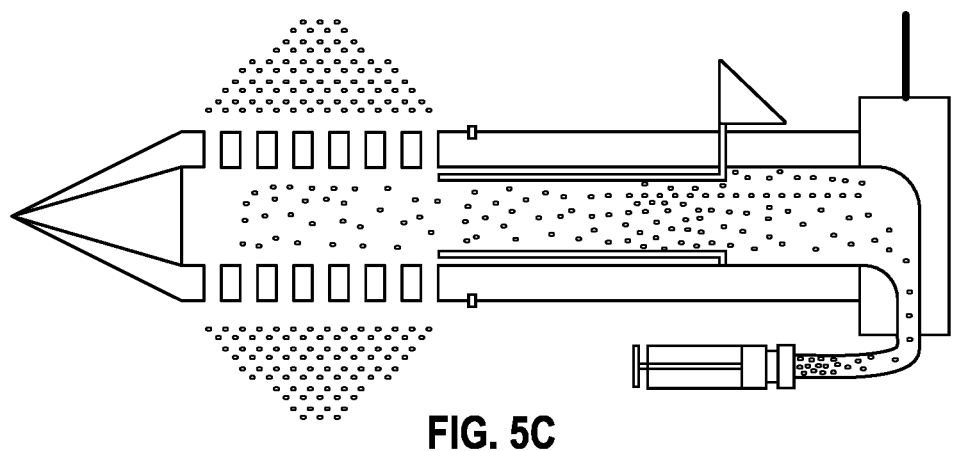
Figure 6:
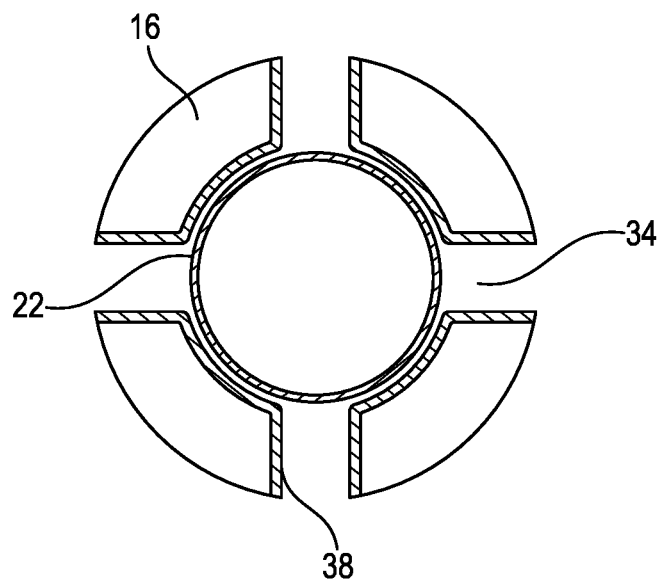
Figure 7:
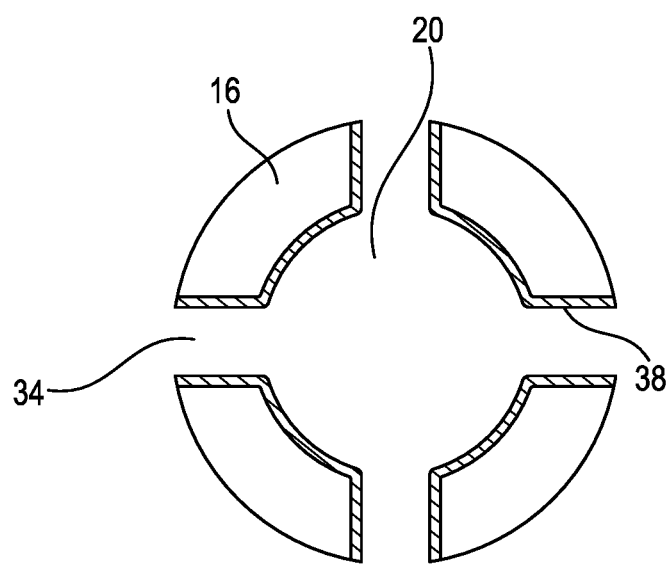

One embodiment of a moveable sleeve that moves between a proximal and a distal position, or up and down, within the internal chamber 20 of the probe is shown in FIGS. 5A-5C. This embodiment of a sleeve 22 may be a solid material configured to slide up and down within the internal chamber. Referring to FIG. 5B, the perforations 34 are sealed from the internal chamber 20 that is filled with an aqueous solution by the presence of the sleeve 22. The sleeve 22 has a lever or tab 24 that is attached to the body of the sleeve. Thus, whenever the tab is pulled upward the sleeve is also pulled upward and the fluid in the internal chamber 20 can flow outward through the perforations as shown in FIG. 5C. FIG. 6 shows a diametrical cross-section of the probe with the sleeve 22 in its closed or distal position sealing the perforations 34 from the internal chamber 20. FIG. 7 shows a diametrical cross-section of the probe with the sleeve 22 in its second or proximal position opening the perforations.

Figure 8A:
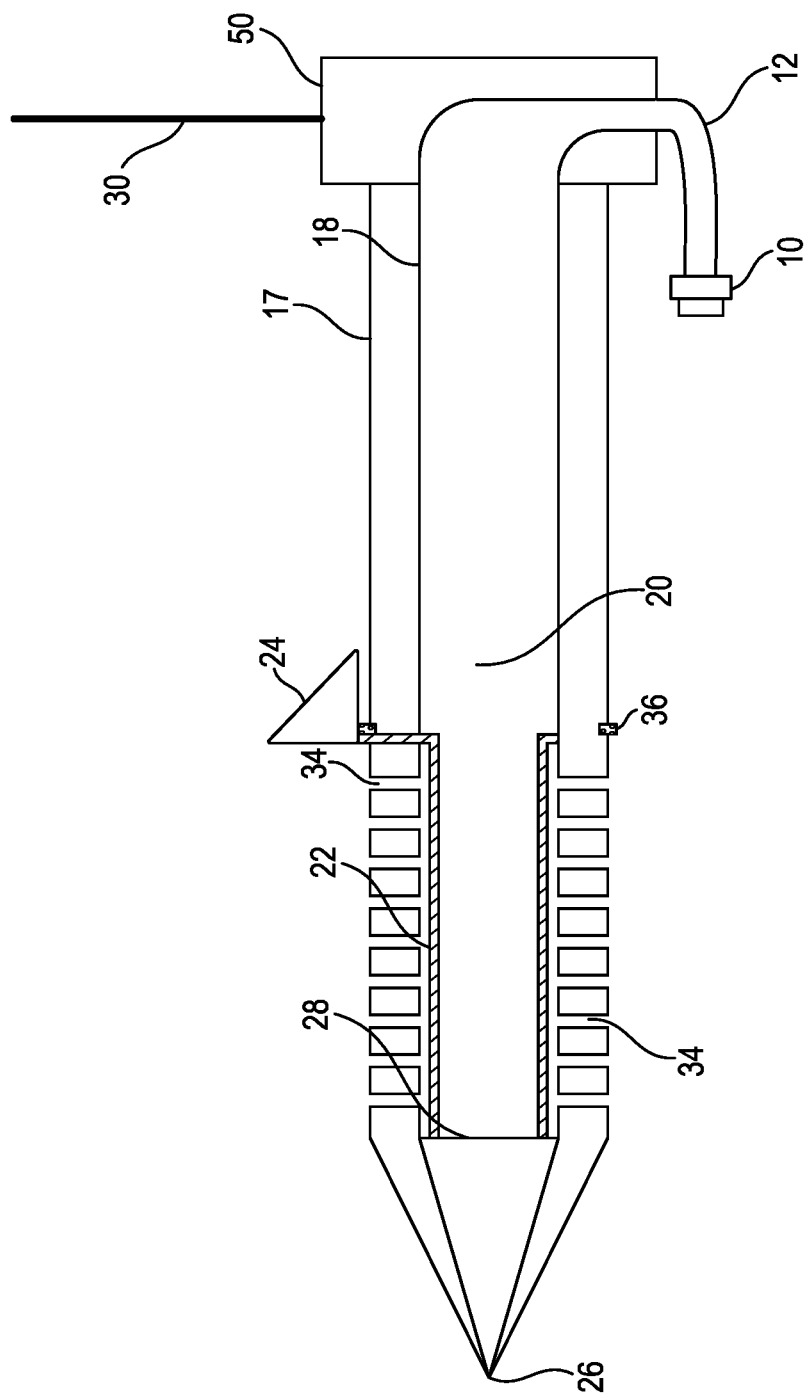
FIGS. 8A-8B are cross-sectional views of the probe demonstrating an alternative method for exposing the internal chamber of the probe to perforations via a rotational mechanism.
Figure 8B:
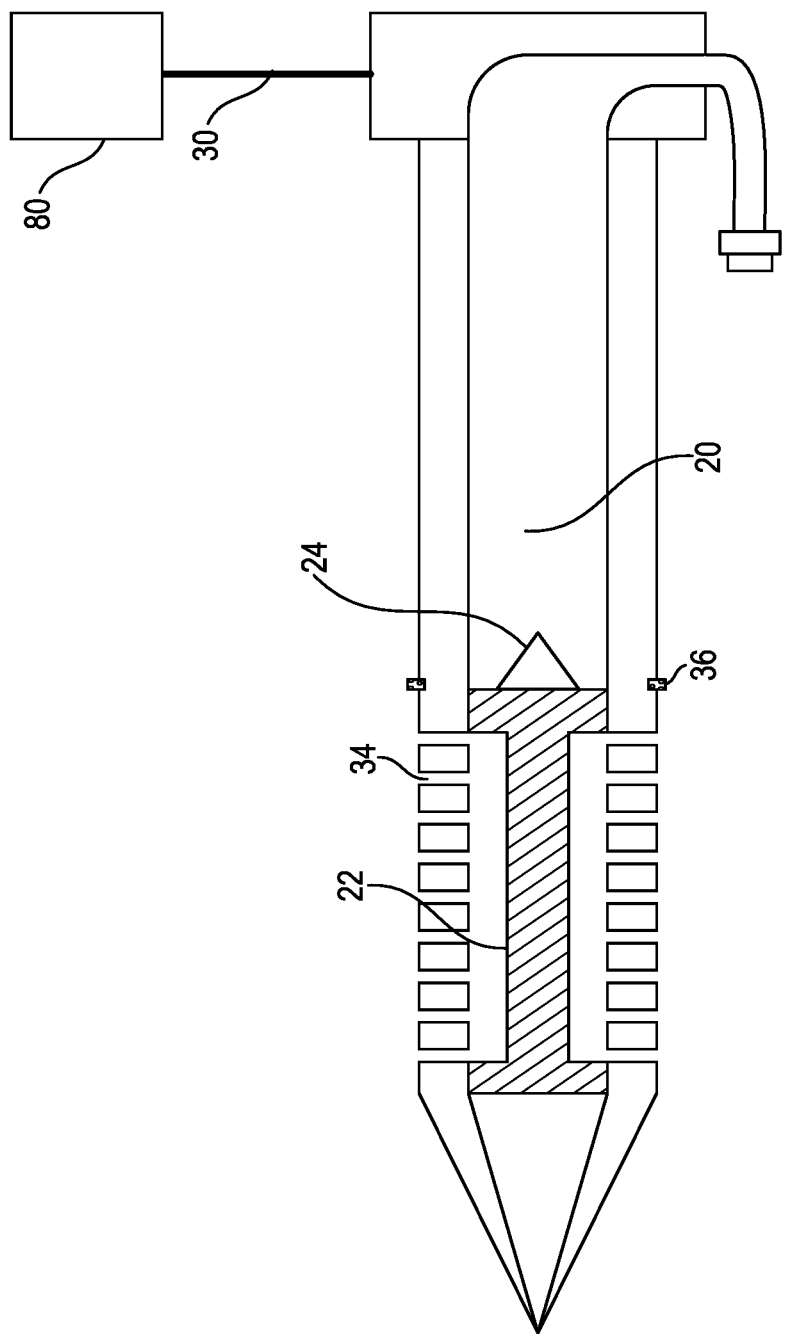
Figure 9A:
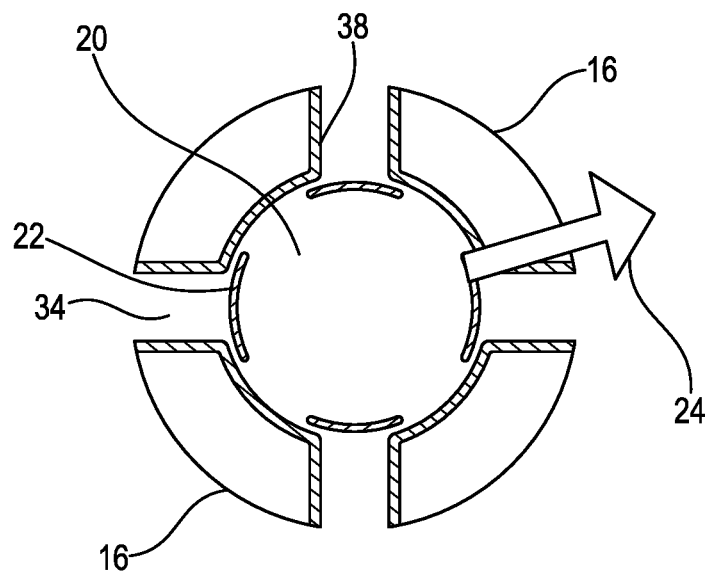
FIGS. 9A-9B are cross-sectional views of the probe along its diameter demonstrating how the rotation of the sleeve shown in FIGS. 8A and 8B can seal or expose the internal chamber of the probe to the perforations.
Figure 9B:
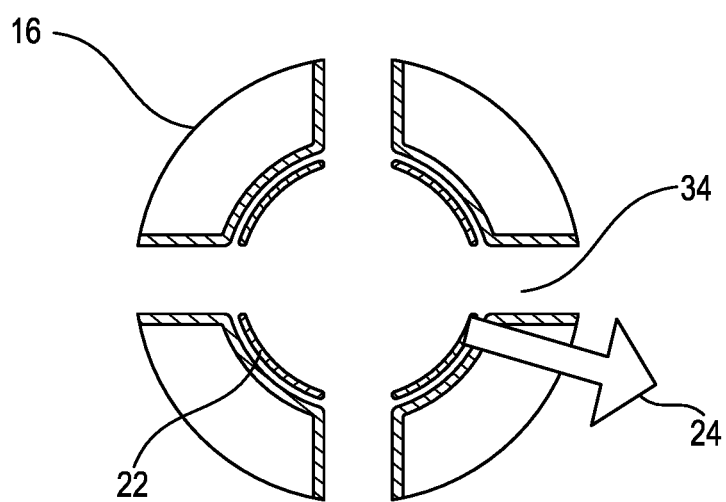
Figure 10:
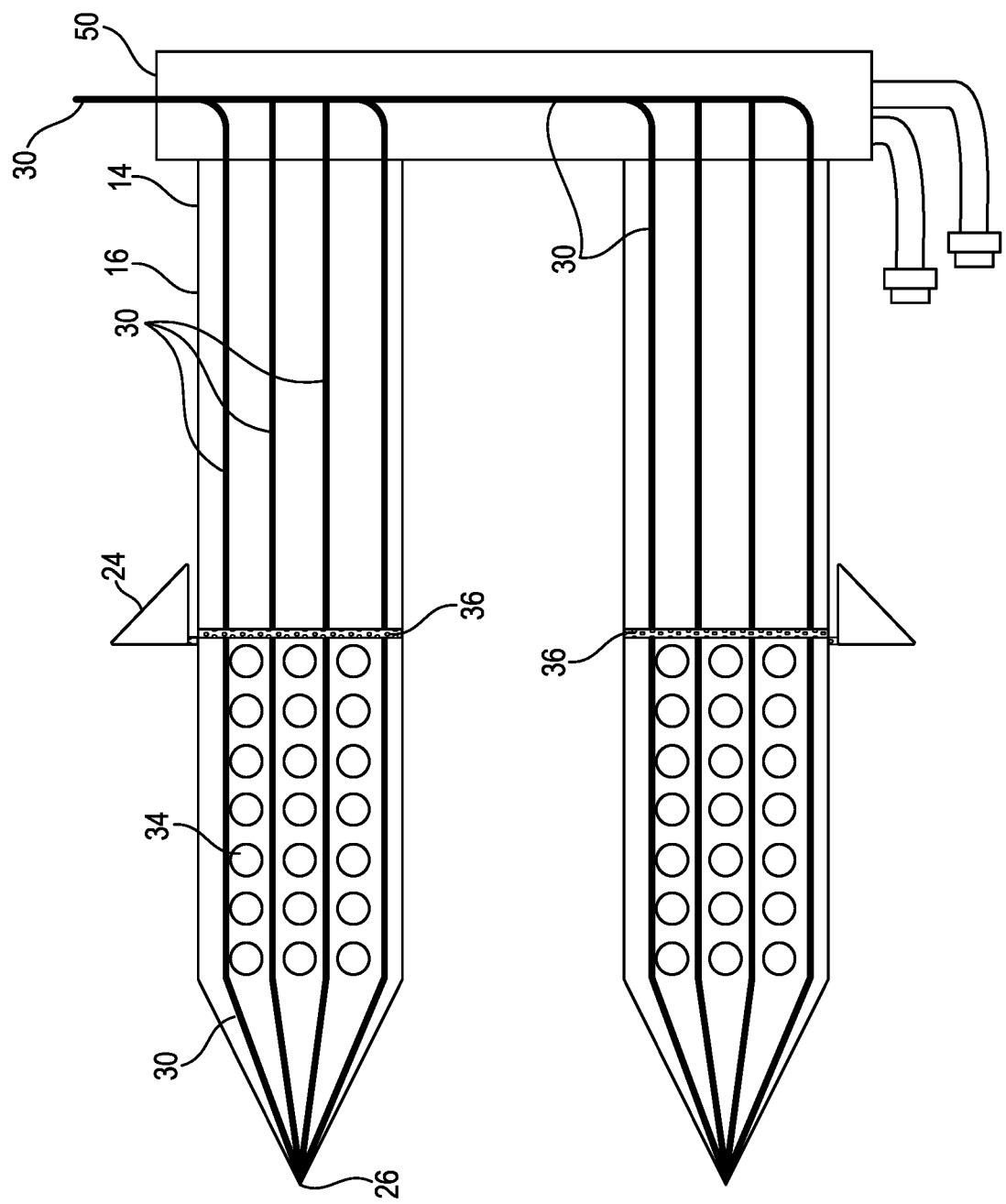

Another embodiment of a moveable sleeve that rotates within the internal chamber 20 is shown in FIGS. 8A-8B. In this embodiment the sleeve 22 has perforations that when aligned with the perforations of the probe body allow the contents of the interior bore of the sleeve to exit through the perforations of the probe body. Referring to FIG. 8A, the perforations 34 are blocked from the internal chamber 20 that is filled with an aqueous solution by the presence of a solid portion of the sleeve 22. When the sleeve tab 24 is rotated, it rotates the sleeve within the internal chamber to a position where matching perforations on the sleeve are aligned with the perforations in the probe body (see FIG. 8B) and the fluid in the sleeve bore or internal chamber 20 may exit through the perforations in the probe body. FIGS. 9A and 9B show diametrical cross-sections of the probe with the solid portion of the sleeve sealing the perforations in the probe body (FIG. 9A) and where the sleeve has been rotated to align the two sets of perforations. (FIG. 9B).

Connector Housing

A connector housing 50 can be used to cap the first end of one or more probe bodies 16 such as illustrated in FIGS. 1-4, and FIGS. 10-12B. The connector housing has one or more connection points that are selectively mateable with one or more probes. When probes are properly mated to the connection points, one or more electrodes 30 and tubings 12 will be properly aligned to ensure their proper connections to the electrodes in the probe body 16 and to the internal chamber 20 respectively.

Each probe body contains one or more electrodes 30 and perforations 34. The distal ends of the electrodes are embedded in the probe body and the proximal ends of the electrodes are connected to an electroporation device. The electrodes pass from the probe body through the connector housing to the electroporation device 80 through the connector housing 50.

Figure 12A:
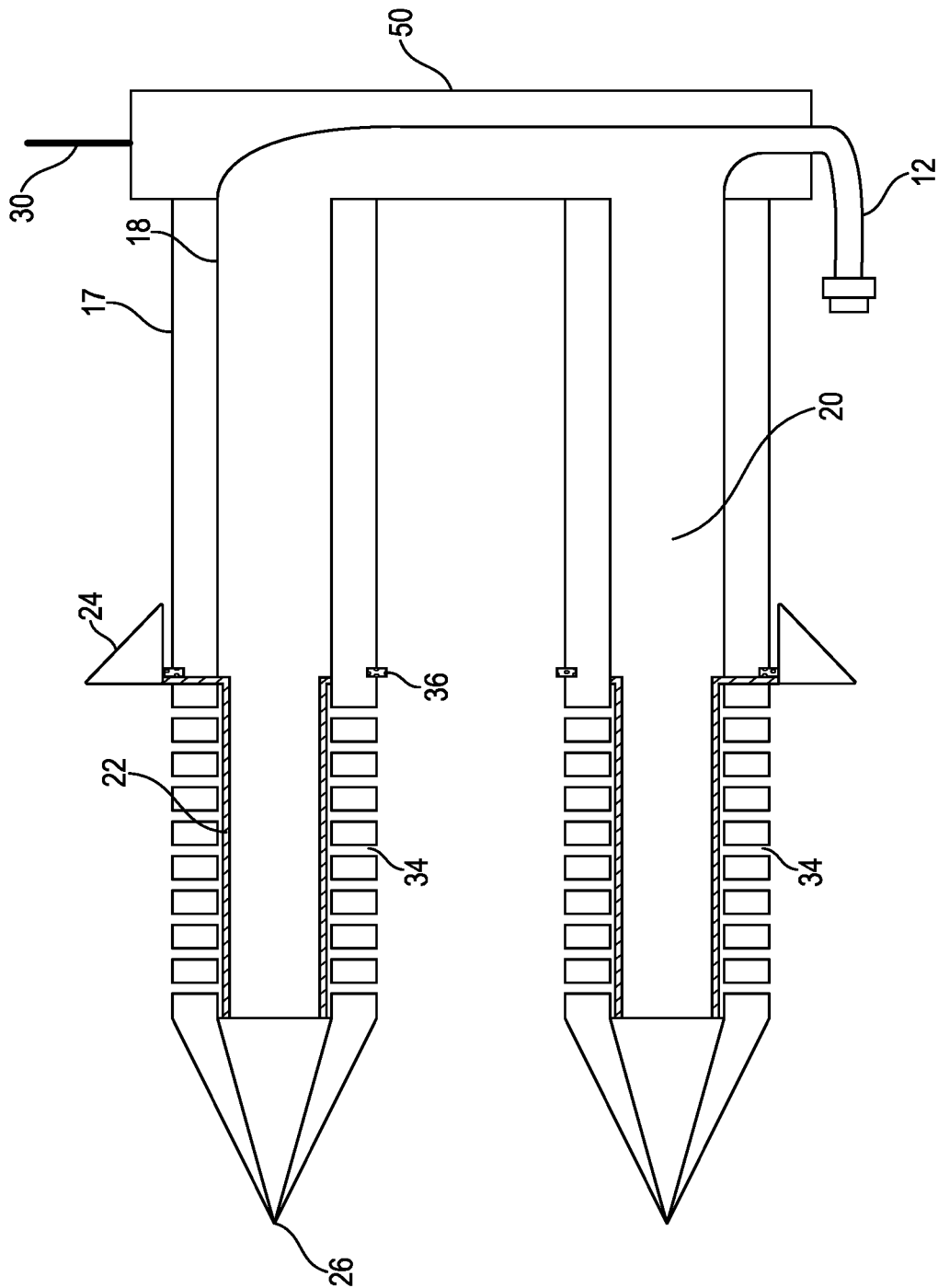
FIGS. 12A-12B are cross-sectional views of a device containing multiple probes, demonstrating the mechanism by which the sleeve of each probe separates the internal chamber of that probe from the perforations, and how the vertical movement of the sleeve allows for exposure of the internal chamber to the perforations.
Figure 12B:
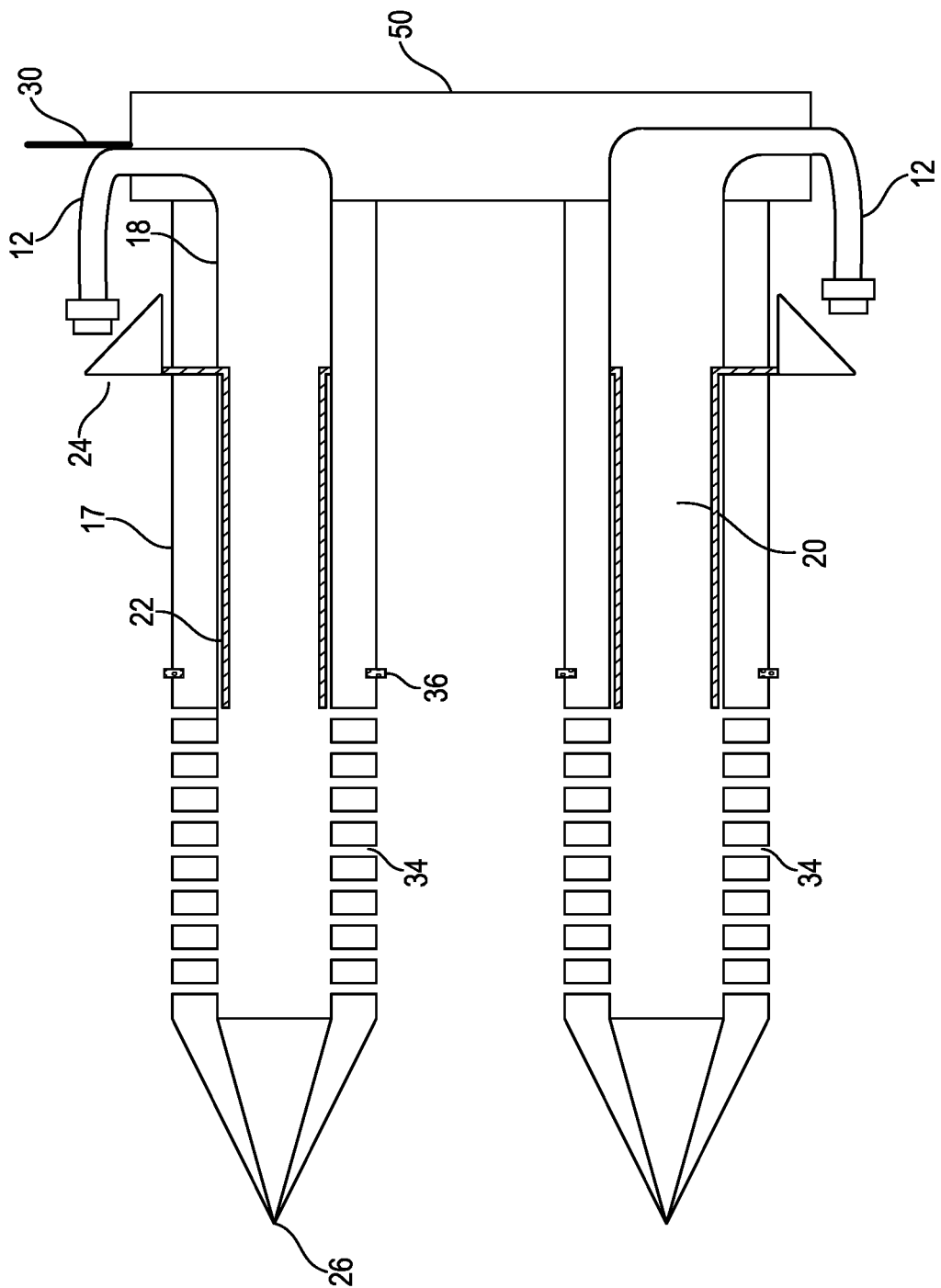
Figure 13A:
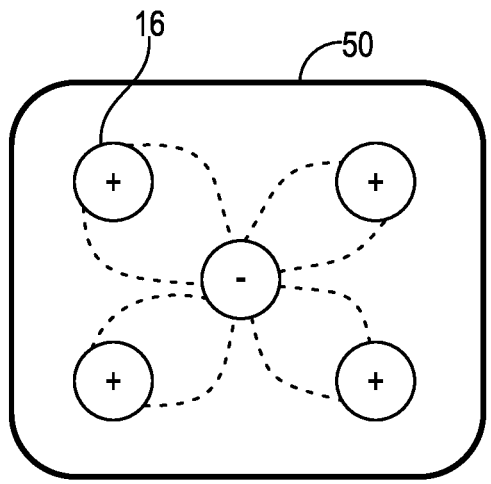
FIG. 13A-13D illustrate the flow of current between different arrays of multiple probes with voltage potentials of varying polarities.
Figure 13B:
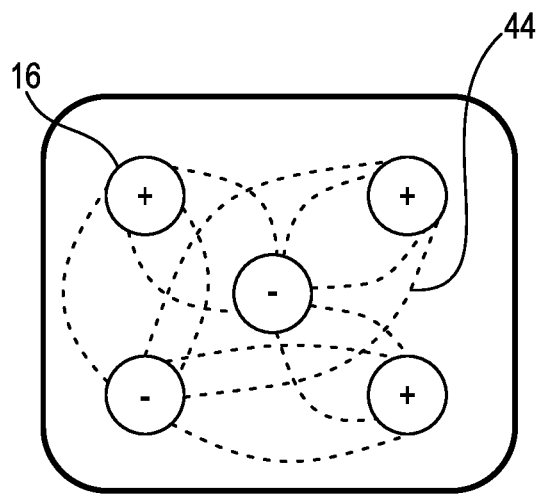
Figure 13C:
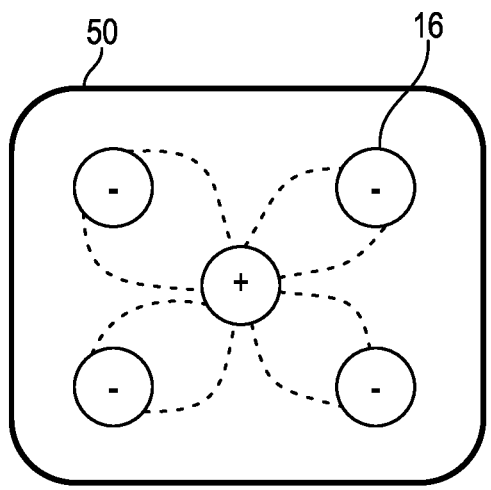
Figure 13D:
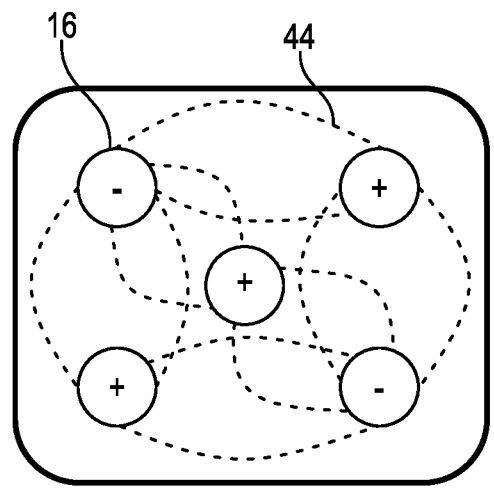

The internal chamber 20 is connected to the tubing 12 to allow fluids to be injected into the internal chamber. Each probe may have its own designated tubing 12 (as shown in FIG. 12B. Alternatively, several probes may be connected to the same tubing as shown in FIG. 12A when an array of probes are used to inject the same liquid into the surrounding tissue. Thus, when the perforations are open a fluid can be injected into the internal chamber and out through the perforations and into the surrounding tissue or target mass as shown in FIGS. 5A-5C.

The liquid injected can be a variety of aqueous materials including but not limited to polar and nonpolar liquids, fluid medications, and any other materials that can be suspended into an aqueous solution including genetic materials, antibodies, nanoparticles, and embolic materials. The internal chamber 20 can connect with the tubing 12 anywhere along the length of the probe. The tubing 12 can be made out any material that allows for the transportation of aqueous solutions including but not limited to plastic, silicone, and silastic materials.

One embodiment of the connector housing 50 can be manufactured to have a set array of probe bodies 16 attached to a connector housing with the appropriate electrode connections and tubing connections in place. Each probe body will have one or more electrodes embedded within the probe body that will pass either a positive or a negative charge to the probe body 16. Examples, of several different probe arrays and their charges, as well as the current 44 passing between the probe bodies of different charges, are seen in FIGS. 13A-13D.

Figure 11:
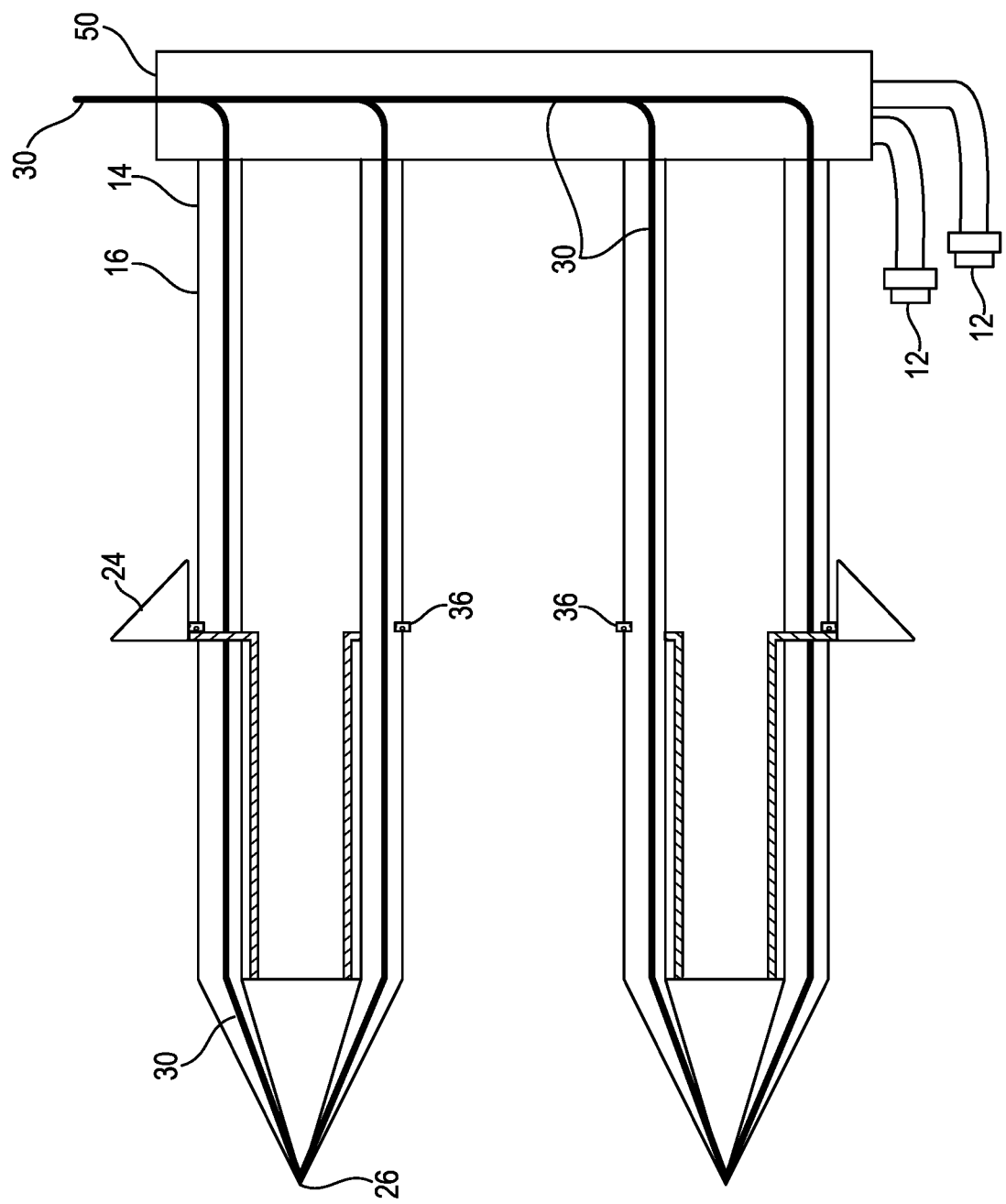

Another embodiment of the connector housing 50 has an array of connection points, wherein each connection point can be easily attached to a probe body. The probes that are attached or mated to the connection points may be the same, similar, or different. Once a probe body is connected to a connection point then one or more electrodes embedded in the probe body will be aligned and in communication with one or more electrodes in the connector housing 50 as shown in FIG. 11. Similarly, whenever a probe body is connected to a connection point then a tubing 12 that passes through the connector housing will be aligned and in communication with the internal chamber of the probe body as shown in FIGS. 12A and 12B.

One or more probe bodies may be deployed from the connector housing in order to stabilize a probe, act as additional independent electrodes, and/or act as hollow-needle injection devices for the injection of aqueous solutions. The deployed probe bodies may all be the same length or they may vary in length. The probe bodies may be selectively deployed from the external surface of the connector housing via a multitude of controllable mechanisms. Such mechanisms include but not limited to a sliding mechanism, clicking mechanism, rotational mechanism, or a button located on the external surface of the probe that activates an electrical, magnetic, mechanical movement, or internet-of-things mechanism for the deployment of the selected probe body from the external surface of the connector housing. Such deployment mechanisms may be controlled via an external remote control device or a wire or connector tethered to the connector housing or the probe bodies that activate such deployment mechanisms. Alternatively, probe bodies may be permanently attached to the connector housing.

Under the command of a standard electroporation machine that allows for the facilitation of electroporation activity, each probe can be programmed to elicit either a positive or negative charge at any number of different voltages, corresponding electrical field strengths, pulse numbers, pulse lengths, intervals between pulses, and polarities. For example, the voltage of the probes can be programmed to a voltage ranging from 0 V/cm to 25000 V/cm depending on the distance between probes; pulse numbers can be programmed to range from 0 to 300; the pulse lengths may be programmed from 0.001 ms to 50000 ms; and the intervals between pulses may be programmed from 0.001 ms to 50000 ms. For example, the current elicited by the probes may include but are not limited to direct current, alternating current, unipolar current, bipolar current, or a number of multipolar currents.

The foregoing provides a detailed description of the invention which forms the subject of the claims of the invention. It should be appreciated by those skilled in the art that the general design and the specific embodiments disclosed might be readily utilized as a basis for modifying or redesigning a chemical and acid storage system to perform equivalent functions, but those skilled in the art should realize that such equivalent constructions do not depart from the spirit and scope of the invention as set forth in the appended claims.

What is claimed is:

1. An electroporation probe comprising:
   (a) a cylindrical probe body having an interior channel, a first proximal end, and a second distal end, and including in its interior an immune checkpoint inhibitor;
   (b) at least seven apertures passing through the probe body and at least four of said apertures located around the probe body such that they are each positioned at 90 degrees from the adjacent apertures when the cylindrical probe body is viewed from its end;
   (c) a sleeve positioned within the interior channel, wherein the sleeve is rotatable on its longest axis between a first position sealing a series of perforations in the interior channel of the sleeve and a second position aligning the perforations with said apertures in the interior channel;
   (d) a fluid channel in fluid communication with the sleeve interior whereby whenever the sleeve is in the second position a fluid injected into the sleeve interior exits through all the apertures in the probe body; and
   (e) one or more electrodes connected with wires running from the distal end to the proximal end and said electrode is connected to an electroporation machine which provides electric pulses to the electrodes ranging from 0 to 2500 V/cm, said pulses having a length 0.001 ms to 50,000 ms and intervals between pulses from 0.001 ms to 50,000 ms.

2. The electroporation probe of claim 1 wherein the sleeve and the fluid channel are substantially the same length.

3. The electroporation probe of claim 1 wherein when the sleeve is in the second position, the fluid from the fluid channel also enters the interior channel and exits through all the apertures in the probe body.

4. The electroporation probe of claim 1 wherein there are nine apertures passing through the probe body.

5. The electroporation probe of claim 1 wherein a tubing provides the fluid to the sleeve interior.

6. The electroporation probe of claim 1, wherein the proximal end of the probe body is provided with one portion of a luer lock connector.

7. The electroporation probe of claim 6, wherein said portion of the luer lock connector is the female portion.

8. The electroporation probe of claim 1, wherein at least a portion of each electrode is covered by an electronically non-conductive material.

9. The electroporation probe of claim 1, wherein one or more of the electrodes are embedded in the probe body.

10. The electroporation probe of claim 1, wherein one of the electrodes is connected to a positive or cathode power source.

11. The electroporation probe of claim 1, wherein one of the electrodes is connected to a negative or anode power source.

12. An electroporation device comprising:
    (a) an electroporation probe having
       (i) a cylindrical probe body having an interior channel, a first proximal end, and a second distal end, and including in its interior pro-inflammatory cytokines or oncolytic agents;
       (ii) at least seven apertures passing through the probe body in the region of the probe body closer to the distal end than the proximal end, and at least four of said apertures located around the probe body such that they are each positioned at 90 degrees from the adjacent apertures when the cylindrical probe body is viewed from its end;
(iii) a sleeve positioned within the interior channel that is moveable between a first position sealing the apertures from the interior channel and a second position opening the apertures to the interior channel,
(iv) at least one electrode embedded in the probe body, and
(b) an electroporation machine in electrical communication with the electrode embedded in the probe body and the sleeve is in fluid communication with the interior channel wherein the electroporation machine provides electric pulses to the electrode ranging from 0 to 2500 V/cm, said pulses having a length 0.001 ms to 50,000 ms and intervals between pulses from 0.001 ms to 50,000 ms.

13. The electroporation probe of claim 12 wherein the sleeve is rotatable between the first position and the second position.

14. The electroporation probe of claim 12 wherein the sleeve and the interior channel are substantially the same length.

15. The electroporation probe of claim 12 wherein there are nine apertures passing through the probe body.

16. The electroporation probe of claim 12 wherein the fluid from the interior of the sleeve exits through the apertures in the probe body.

17. The electroporation probe of claim 12 wherein the proximal end of the probe body is provided with one portion of a luer lock connector.

18. The electroporation probe of claim 17, wherein said portion of the luer lock connector is the female portion.

19. The electroporation probe of claim 12, wherein at least a portion of the electrode is covered by an electronically non-conductive material.

20. The electroporation probe of claim 12, wherein the electrode is connected to a positive or cathode power source.

21. The electroporation probe of claim 20, wherein the electrode is connected with wires around the outer portion of the probe body.

22. The electroporation probe of claim 12, wherein the electrode is connected to a negative or anode power source.

23. The electroporation probe of claim 22, wherein the electrode is connected with wires around the outer portion of the probe body.

24. The electroporation probe of claim 12, wherein a radio-opaque marker is positioned on the probe body at the proximal end of the probe body.

25. The electroporation probe of claim 12, wherein a radio-opaque marker is positioned on the probe body at the distal end of the probe body.

26. The electroporation probe of claim 12, wherein a radio-opaque marker is positioned proximal to the perforation closest to the proximal end.

* * * * *